United States Patent [19]

Langley

[11] Patent Number: 5,447,863
[45] Date of Patent: Sep. 5, 1995

[54] METHOD FOR PURIFYING ISLETS OF LANGERHANS

[75] Inventor: Robert W. Langley, Westminster, Colo.

[73] Assignee: COBE Laboratories, Inc., Lakewood, Colo.

[21] Appl. No.: 126,492

[22] Filed: Nov. 2, 1993

Related U.S. Application Data

[62] Division of Ser. No. 853,092, Mar. 18, 1992, Pat. No. 5,273,904.

[51] Int. Cl.$^6$ .............................................. C12S 3/24
[52] U.S. Cl. ...................................... 435/268; 435/803
[58] Field of Search .................. 435/2, 262, 267, 268, 435/287, 288, 803; 210/632, 800, 803, 804, 739, 740, 745, 513, 511, 532.1, 534; 209/157; 422/44, 101

[56] References Cited

U.S. PATENT DOCUMENTS

| | | | |
|---|---|---|---|
| 1,048,171 | 12/1912 | Hughes | 209/157 |
| 2,009,559 | 7/1935 | Mieder | 210/532.1 |
| 2,142,888 | 1/1939 | Donnallan | 210/513 |
| 3,494,475 | 2/1970 | Hedstrom et al. | 209/157 |
| 3,552,554 | 1/1971 | Olgard | 210/519 |
| 3,709,361 | 1/1973 | Miller | 210/511 |
| 4,424,132 | 1/1984 | Iriguchi | 210/800 |
| 4,765,899 | 8/1988 | Wells et al. | 422/44 |
| 4,868,121 | 9/1989 | Scharp et al. | 435/268 |
| 5,079,160 | 1/1992 | Lacy et al. | 435/268 |

FOREIGN PATENT DOCUMENTS

| | | | |
|---|---|---|---|
| 3631267 | 3/1988 | Germany | 435/287 |
| 1659470 | 6/1991 | U.S.S.R. | 435/287 |

*Primary Examiner*—William H. Beisner
*Attorney, Agent, or Firm*—Beaton & Folsom

[57] ABSTRACT

A method and apparatus to concentrate and purify islets of Langerhans from a tissue suspension containing islets and tissue fragments. The tissue suspension is flowed through an inclined channel such that laminar flow is established in the channel. The islets settle toward the channel bottom and are drawn out of the channel through an outlet in the channel bottom, while the remaining tissue suspension flows out a second outlet positioned higher than the islet outlet. Additional concentration or purification may be accomplished by passing the islets through the channel additional times and by centrifuging or filtering operations.

12 Claims, 4 Drawing Sheets

METHOD FOR PURIFYING ISLETS OF LANGERHANS

This is a divisional of application Ser. No. 07/853,092 filed on Mar. 18, 1992, now issued as U.S. Pat. No. 5,273,904.

FIELD OF THE INVENTION

This invention relates to a method and apparatus for concentrating and/or purifying islets of Langerhans from a solution containing islets mixed with other matter such as digested or partially digested pancreatic tissue. The viable concentrated and purified islets can then be transplanted into a patient to produce insulin in the patient.

BACKGROUND OF THE INVENTION

Diabetes is a serious and prevalent disease. In the United States alone, over two million people have Type I, Insulin Dependent Diabetes Mellitus, and about eight to ten million people have Type II, non-Insulin Dependent Diabetes Mellitus. Microvascular complications caused by the disease make it the third leading cause of death, the leading cause of new blindness, the cause of kidney failures resulting in 30% of new kidney transplants, a major factor in myocardial infarction and stroke, a leading cause of gangrene and amputation, and an important cause of male impotence. The total monetary impact of the disease in the United States alone is estimated to be around $14 billion a year.

Insulin is produced by islets of Langerhans located in the pancreas. The isolation of islets from a donor pancreas or from an animal pancreas, and the transplantation of those islets into a diabetic patient, may be a viable treatment for diabetes.

By transplanting only purified islets rather than intact pancreatic segments, the transplantation can be accomplished by injecting the islets into the bloodstream so that they lodge in the liver rather than by surgically implanting the pancreatic segments into the patient's pancreas. Intravenous injection of the islets also allows that possibility of treating the islets in vitro to prevent rejection without the necessity of immunosuppression, it avoids problems associated with the secretion of digestive substances by a transplanted pancreas segment, and it allows the possibility of cryopreservation of the tissue for later use and the possibility of xenografts.

The removal of islets from the pancreas to obtain a tissue suspension of islets and pancreatic tissue has been explored at length. The typical procedure is to break down the pancreatic tissue with a digestive enzyme such as collagenase to free the islets. Such procedures are described in a number of scientific publications, including World Journal of Surgery, April 1984 and the Journal of the American Diabetes Association, Vol. lb, No. 1, pp 35-39 "Method for the Isolation of Intact Islets of Langerhans from the Rat Pancreas."

The difficulty with collagenase digestion of the pancreatic tissue to free the islets is that the individual islets are freed at different rates based on their size distribution, concentration and degree of entrainment in the tissue. Therefore, during the time the collagenase is digesting pancreatic tissue to free the unfreed islets, it is also continuing to act on the islets that have already been freed, thereby breaking up the freed islets into smaller groups and even individual cells and degrading those cells. The end result is that the number of viable islets that are freed by this process is much less than the number of islets in the pancreatic sample that is processed.

There has been considerable effort directed toward modifying the basic collagenase digestion process in an attempt to achieve higher effective separation rates. These efforts have included, for example, the use of VELCRO brand hook fasteners to collect tissue fragments (see Diabetes, Vol. 31, Suppl. 4, August 1982, "An Improved Method for the Isolation of Islets from the Beef Pancreas"); teasing and shaking the pancreas to assist in releasing the islets (see Diabetes, Vol. 33, November 1984, "A Method for Isolation of Islets of Langerhans from the Human Pancreas"); dicing the pancreas into small units (see Transplantation Proceedings, Vol. XVII, No. 1 (February), 1985, "Isolation of Human Pancreatic Islets from Cryopreserved Pancreas"); methods for minimizing gelation in the pancreas which tends to trap islets (see Diabetes, Vol. 38, Suppl. 1, January 1989, "Factors Influencing Isolation of Islets of Langerhans"; and controlling the collagenase contents (see Diabetes, Vol. 38, Suppl. 1, January 1989, "Protease Activity in Pancreatic Islet Isolation by Enzymatic Digestion").

Another of these methods to increase islet yield relating to collagenase digestion relies on injecting the collagenase into the pancreas main duct. Such a method using continuous peristaltic ductal perfusion is taught in Transplantation Proceedings, Vol. 22, No. 2 (April), pp. 789-790, "A Simple Method for Bulk Separation of Highly Purified Human Islets of Langerhans". A similar method using spherical agitators in a container to enhance tissue agitation is described in U.S. Pat. No. 4,868,121 by Scharp et al., and in PCT International Application No. WO 88/09667, published Dec. 15, 1988, naming Washington University as Applicant.

Once the islets are separated from the pancreas and isolated in a solution containing islets and partially digested pancreas tissue fragments, there are several techniques for concentrating and purifying the tissue suspension. The most common includes concentrating the solution and then centrifuging the solution with a medium solution such as a Ficoll or Percoll gradient so that the islets can be isolated and drawn off from the solution and from the tissue fragments. Such methods are described in some detail in, for example, Transplantation, August 1976, pp. 201-205, "The Use of Hypaque-Ficoll in the Isolation of Pancreatic Islets in Rats"; Biochemical and Biophysical Research Communications, Vol. 79, No. 3, 1977, p. 823, "Rapid Isolation of Pancreatic Islets from Collagenase Digested Pancreas by Sedimentation through Percoll at Unit Gravity"; Endocrinal, 1981, 28(5), pp. 563-567, "A Rapid Method for the Separation of Rat Pancreatic Islets from Collagenase-Digested Pancreas using Percoll"; Transplantation, Vol. 43, No. 6, pp. 805-808, "Bovine Serum Albumin Density Gradient Isolation of Rat Pancreatic Islets"; Transplantation Proceedings, Vol. 22, No. 2 (April), 1990, pp. 758-8759, "Human Pancreatic Islet Isolation with Increased Incubation Temperatures and Variable Density Gradients"; Transplantation Proceedings, Vol. 22, No. 2 (April) 1990, pp. 789-709, "A Simple Method for Bulk Separation of Highly Purified Human Islets of Langerhans."

Other techniques for concentration and purification use filtering, either alone or in combination with centrifuging. See, for example, Diabetes, Vol. 25, No. 8, pp. 667-672, "Standardization of a Digestion-Filtration Method of Isolation of Pancreatic Islets"; Diabetes, Vol. 33, November 1984, "A Method for Isolation of Islets of Langerhans from the Human Pancreas"; Diabetes, Vol. 33, November 1984, "A Method for Isolation of Langerhans from the Human Pancreas"; and Diabetes, Vol. 35, June 1986, "A Method for the Mass Isolation of Islets from the Adult Pig Pancreas". Also, see the Scharp patent and Washington University published PCT application referenced above.

Both the centrifuging and filtering processes have drawbacks. Both are fairly time-consuming. They are also somewhat variable in the results they achieve, in view of the differences normally encountered from batch to batch of islet-containing solutions. Also of importance is that islets are thought to be quite fragile, and both centrifuging and force-filtering may damage the islets and degrade their viability.

As explained in detail below, the present invention partially concentrates the islets by using gravity sedimentation of islets through an inclined channel with a collection well at the bottom. The partially concentrated islets can then be further concentrated with a minimum of ordinary centrifugation or filtering or other processes known in the art. Although the general concept of gravity sedimentation of suspended solids through an inclined channel is well-known, it is believed that such an approach has never been adopted for the processing of islets. U.S. Pat. No. 4,765,899 by Wells et al. describes an apparatus for continuously separating blood components which utilizes a disk-shaped chamber with a central inlet and circumferential upper and lower outlets. In the Wells method, solids do not in fact fall to the bottom of the container, but the fluid is merely stratified into fractions. Moreover, the configuration and flow parameters are designed for blood separation, and nothing in the Wells patent suggests using the Wells apparatus to attempt islet processing. Another patent, U.S. Pat. No. 4,424,132 by Iriguchi, describes a non-inclined chamber having an inlet at one end and upper and lower outlets at the other end to stratify blood components. As in the Wells patent, the configuration and flow parameters are designed for blood separation, and nothing in the patent suggests using any such apparatus for islet processing.

SUMMARY OF THE INVENTION

The present invention is an economical and effective apparatus and method to concentrate and purify islets from a tissue suspension containing islets and tissue fragments, by flowing the tissue suspension through an inclined channel. The inclined channel has a tissue suspension inlet at the top end and a tissue suspension outlet and an islet outlet at the bottom end. Islets sediment onto the floor of the channel and flow down the floor and into a collection well. The islet outlet is at the bottom of the collection well. The flow parameters are such that laminar flow is established and maintained through the channel to allow sedimentation and to prevent re-entrainment of the islets after they sediment onto the channel floor, and the flow rates in the inlet and two outlets is such that the concentration of islets in the discharge from the islet outlet is much higher than in the inlet tissue suspension. The islet outlet discharge can then be purified further if desired by conventional gradient medium centrifugation or filtration or both.

The invention lessens the trauma to the islets caused by prolonged centrifugation or high pressure filtering processes. As compared to procedures that rely on some combination of filter or centrifugation, it is also simpler, less expensive, much less labor intensive, and lends itself better to automation and aseptic processing.

The system may include one or more pumps upstream from the inlet, downstream from the tissue suspension outlet, downstream from the islet outlet, or any combination of those. The pumps may be controlled with preselected flow parameters and may be controlled with the use of one or more weighing devices or measurement means to measure the volume and flow rates through the inlet and outlets. The system may provide for additional purification by passing the discharge from either outlet through the channel multiple times. It may also provide for additional purification by flowing Hanks solution or similar uncontaminated solution through the channel and injecting the islet outlet discharge into the upper lamina of that flow to allow unhindered sedimentation of the islets.

DETAILED DESCRIPTION OF THE INVENTION

Figure 1:
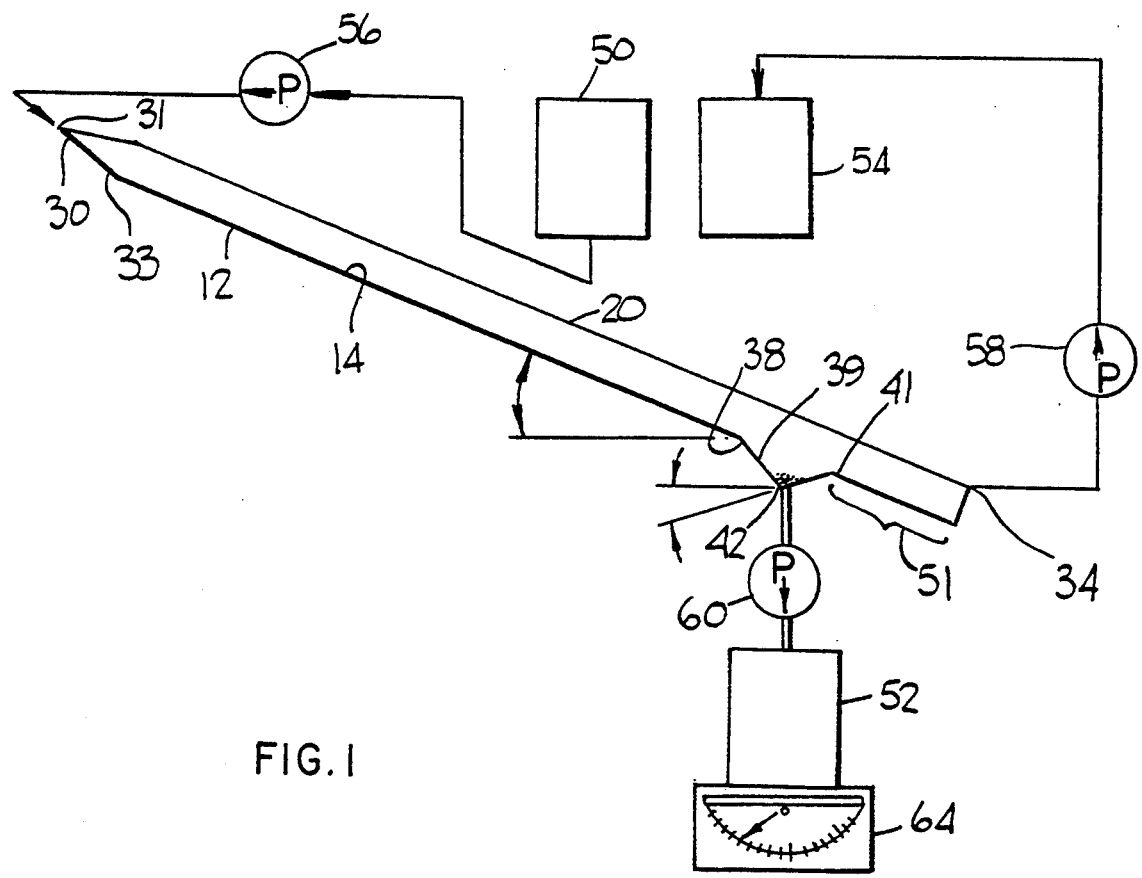
FIG. 1 is a diagrammatic representation of the invention.
Figure 2:
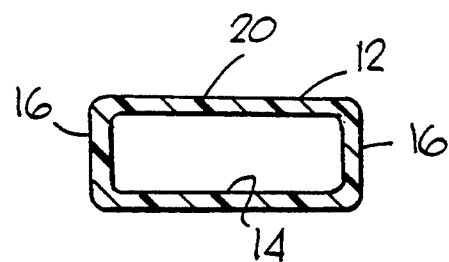
FIG. 2 is a cross-sectional view of the flow channel of the invention.

The invention 10 is shown diagrammatically in FIGS. 1 and 2. It includes an inclined flow device such as a channel 12 that is preferably of a rectangular cross-section with a flat floor 14, two sides 16 that are substantially parallel to one another and perpendicular to the floor, and a top 20. At the upper end of the channel 12 is an inlet 30 and at the lower end of the channel is a tissue suspension outlet 34, a collection well 38 in the channel floor 14, and an islet outlet 42 in the bottom of the collection well. Although the flow device is described as a channel with a rectangular cross section, it will be apparent to those skilled in the art that other cross sections may also be feasible. Preferably, the flow device is at least some type of conduit through which the tissue suspension can travel.

The collection well 38 has an upstream wall 39 and a downstream wall 41. The upper ends of the upstream wall 39 and downstream wall 41 join the channel floor 14, and the lower ends of the upstream wall 39 and downstream wall 41 abut the islet outlet 42. The downstream wall is inclined with the upper end higher than the lower end so that any islets that collect on the downstream wall slide down the wall and out the islet outlet 42.

Downstream from the collection well 38 and upstream from the tissue suspension outlet 34 is a short flow segment 51. This segment 51 prevents flow disturbances from propagating upstream from the outlet to the collect well 38.

A tissue suspension storage chamber 50 is in fluid communication with the inlet 30, an islet collection chamber 52 is in fluid communication with the lower outlet 42, and a processed tissue suspension collection chamber 54 is in fluid communication with the tissue suspension outlet 34. These chambers may be plastic bags. One or more scales or other measuring devices may be used to compute the rate or volume of inlet flow or the discharge from the islet outlet or tissue suspension outlet, such as the scale 64 of FIG. 1.

The flow may be accomplished with any, all or some combination of an inlet flow pump 56, a tissue suspension outlet flow pump 58, and an islet outlet flow pump 60. In one embodiment, there is only an inlet flow pump 56 and islet outlet flow pump. In another embodiment, there is only an inlet flow pump 56 and tissue suspension outlet flow pump 58. The rates of flow out of the tissue suspension storage chamber 50 and into the islet collection chamber 52 and the processed tissue suspension collection chamber 54, can be adjusted by these various pumps.

In one embodiment, the channel 12 is a plastic extrusion having an inner width of about 3.2 cm, an interior height of about 0.6 cm, and a length of about 90 cm. The channel is inclined at 20° to 60°.

In operation, the tissue suspension is placed into the tissue suspension storage chamber 50 in fluid communication with the inlet 30, and an islet collection chamber 52 and processed tissue suspension collection chamber 54 are put in fluid communication with the islet outlet 42 and tissue suspension outlet 34, respectively. A pump such as the inlet flow pump 56 is activated to draw tissue suspension out of the tissue suspension chamber 50 and into the channel 14 through the tissue suspension inlet 30. The tissue suspension flows down the interior of the channel 12. The islets settle to the channel floor 14 faster than the tissue fragments, due to the larger relative diameter of the islets. As the islets and tissue reach the channel floor, they migrate down the inclined floor in a thin layer until they reach the collection well 38, where they are drawn off into the islet collection chamber 52. It has been found that an "air rinse" process may be desirable after the tissue suspension has been processed through the channel. This involves pumping air through the channel using the pump that ordinarily pumps the tissue suspension, in order to rinse the islets off the channel bottom and out the collection well.

The sedimentation process is normally conducted with the channel completely purged of air. Therefore, there is a step at the outset of venting the air through a vent (not shown) or otherwise freeing the air and filling the channel with liquid.

The islets collected in the islet collection chamber can then be separated from the tissue fragments that remain by using centrifugation techniques with a gradient medium, or filtration, or both. Although the final step of centrifugation or filtration may still be required, it is now much easier to perform because most of the tissue has been separated out, and also because the total volume of tissue suspension to be processed has been greatly reduced.

Several variations on the basic inclined channel design are possible. For example, the processed tissue suspension collection chamber 54 may have a return line (not shown) to the storage chamber 50 so that processed tissue suspension can be reprocessed to further increase islet purity. The islet collection chamber 52 may also have a return line (not shown) to reprocess and further purify or concentrate the islets collected in the islet collection chamber 52. In yet another variation, the processed islets drawn out of the islet outlet are introduced into the top of a flow of Hank's solution or a similar solution that is flowed through the channel. The point of introduction is preferably near the top of the portion of the channel in which laminar flow is established so that the differential sedimentation between islets and tissue fragments is enhanced by requiring both to sediment through the entire channel height to the channel floor. Finally, a centrifuge or filtering system may be in-line with the outlet.

One very important constraint regarding the dimensions and flow parameters of the system is that the flow down the channel is preferably fully laminar. This is so that islet sedimentation is not negated by turbulence and so that islets that settle to the channel floor are not re-entrained into the solution. Instead, the islets sediment to the bottom of the channel 12 and migrate down the inclined channel floor 14 into the collection well where they can be drawn off by the islet outlet 42. Laminar flow may be achievable with a Reynolds Number less than about 2000.

Assuming a conservative Reynolds Number of about 1000 to be certain that fully laminar flow is established, the other design parameters can be established depending on the desired processing rate. It is known that the sedimentation velocity of a solid suspended in a liquid is proportional to the difference in density between the solid and the liquid and the square of the solid diameter. Of these, the diameter is the predominant variable for solids that have densities close to that of the liquid. It can be calculated that the sedimentation velocity of islets with a density of 1.09 g/cm$^3$ and a median diameter of about 150 microns in saline solution, will be roughly 0.10 cm/sec. Therefore, the average time it would take for an islet to settle from the top of the channel to the channel floor would be:

$$t_s = d_s/(0.10)$$

where:
 $t_s$ = average time in seconds to sediment to the channel floor
 $d_s$ = channel height in cm The average time of residence in the channel is:

$$t_r = V_c/Q$$

where:
 $t_r$ = average time in seconds of residence in the sedimentation channel
 $V_c$ = volume of the channel
 $Q$ = flow rate through the channel in cm$^3$/sec The volume of the sedimentation channel V can be expressed as:

$$V_c = L_s d_s w$$

where:
 $L_s$ = sedimentation length of the channel
 $w$ = width of the channel

If it is desired that practically all the islets sediment to the channel floor as they flow through the channel, then the average time required for an islet to settle from the top of the channel to the channel floor $t_s$ may be set equal to about half the average residence time in the channel $t_r$:

$$t_s = t_r/2$$

so that:

$$d_s/(0.10) = V_c/(2Q)$$

In other words, the average "packing factor" should typically be about 2 or more. Expressing $V_c$ as $L_s\, d_s\, w$ and cancelling out $d_s$:

$$Q = (0.05)L_s w$$

$$Q(\text{ml/min}) = 9.6 L_s(\text{cm}) = 24.4 L_s(\text{in})$$

A notable point about this is that the permissible flow rate is dependent on the sedimentation length of the channel and the width of the channel but is not at all dependent on the sedimentation distance $d_s$ which is the height of the channel. Although a higher channel will carry a greater volume solution at a given velocity, that carrying capacity is offset by the additional distance of sedimentation.

The above expresses the sedimentation length of the channel $L_s$ as a function of the flow rate Q for a given channel width w. To establish laminar flow with a Reynolds Number of 1000, and assuming the hydraulic diameter $d_H$ is twice the sedimentation distance $d_s$, then the maximum flow rate Q can be calculated to be about 16.7 cm³/sec or 1000 ml/min.

The length of channel required to develop laminar flow can be expressed as a function of the Reynolds Number, and the flow rate Q, so that $$L_E(\text{in}) = 0.028 Q(\text{ml/min})$$

where:
$L_E$ = entry length in inches
The total time to process the volume of solution is given by:

$$t_p = V_p/Q$$

where
$t_p$ = total time to process
$V_p$ = volume of solution to be processed

In the example presented above, the average sedimentation time $t_s$ was set equal to half the average residence time $t_r$ so that the average packing factor PF was two. This compensates for the non-uniform laminar velocity profile, non-uniform spatial distribution of particles at the channel entrance, hindered sedimentation caused by high solid concentration in the solution and, in particular, allows the full sedimentation of islets having diameters less than the median of 150 microns assumed in the example. For an average packing factor of two, a process volume of 10 liters, and a collect volume of 30 ml, the following hypothetical parameters can be generated from the above equations (where $Q_w$ = collect rate of islets):

| Q ml/min | $t_p$ (min) | $L_s$ (in) | $L_E$ (in) | $L_{total}$ (in) | $Q_w$ (ml/min) |
|---|---|---|---|---|---|
| 250 | 40 | 10 | 7 | 17 | .75 |
| 500 | 20 | 20 | 14 | 34 | 1.5 |
| 1000 | 10 | 41 | 28 | 69 | 3 |

If exocrine tissue fragments are assumed to have a density of 1.11 g/cm³, and a median diameter of 50 microns, then the packing factor PF for the exocrine tissue fragments in the example above will be 0.28.

The performance parameters in the hypothetical example set forth above do not assume specific distributions of islet diameters and exocrine tissue fragment diameters. In fact, both diameters can be expected to vary in a given tissue suspension. The following hypothetical example assumes specific size distributions.

Islet diameters may generally range from 50 to 500 microns and exocrine tissue fragments from digested pancreas may generally range from about 5 to 100 microns. This example assumes that the size distribution for both islets and tissue are log-normal, as is commonly the case for small particles (including blood platelets), and the above ranges are assumed to correspond to standard deviations of 2.0. The median diameter of islets is 160 microns so that the median sedimentation velocity is 0.114 cm/sec and the range of sedimentation velocities is 0.011 to 1.1 cm/sec. The median diameter of tissue is 20 microns so that the median sedimentation velocity is 0.0022 cm/sec and the range of sedimentation velocities is 0.00009 to 0.056 cm/sec.

Figure 3:
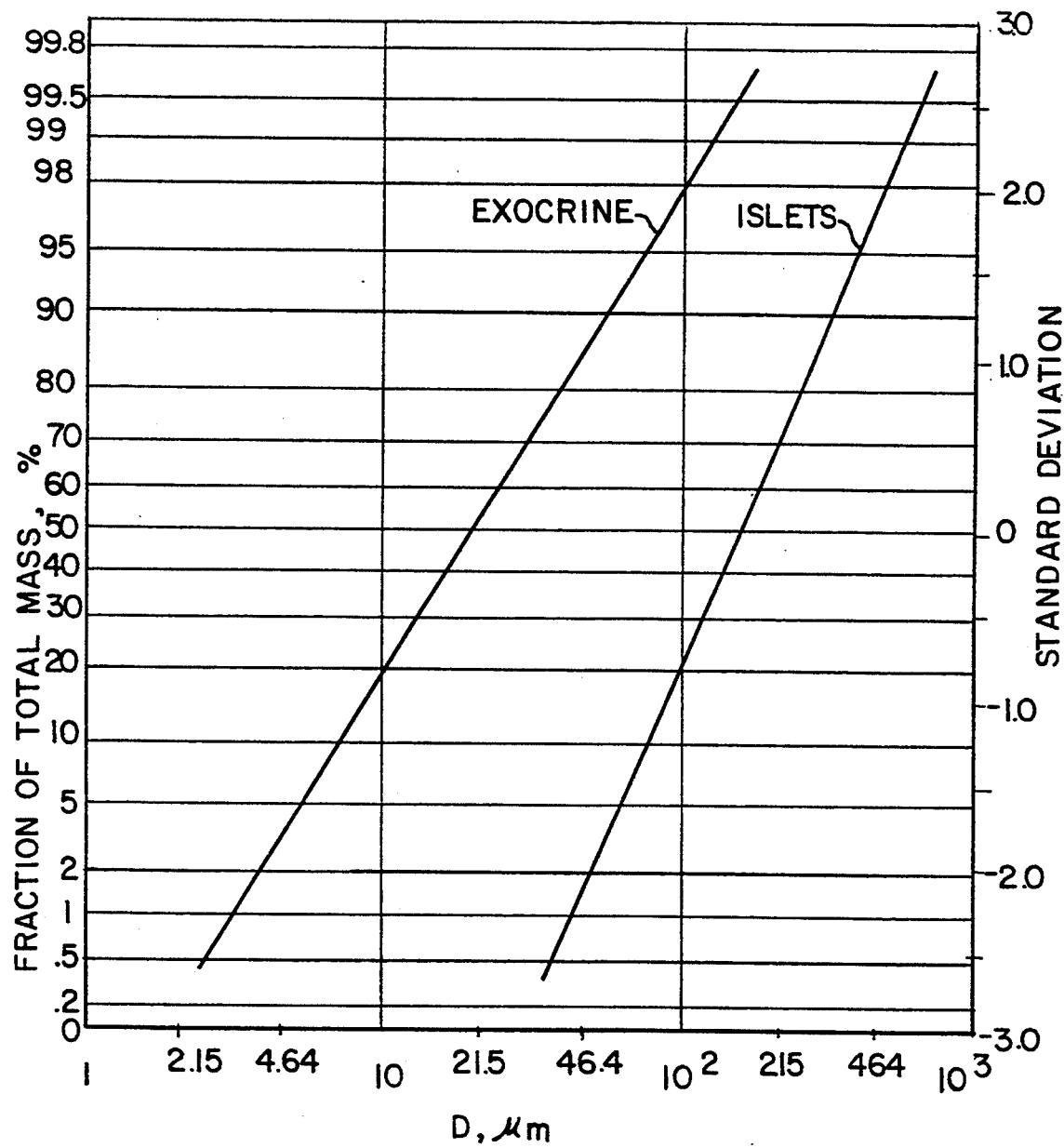
FIG. 3 shows the size distributions of islets and exocrine tissue for the hypothetical example herein.
Figure 4:
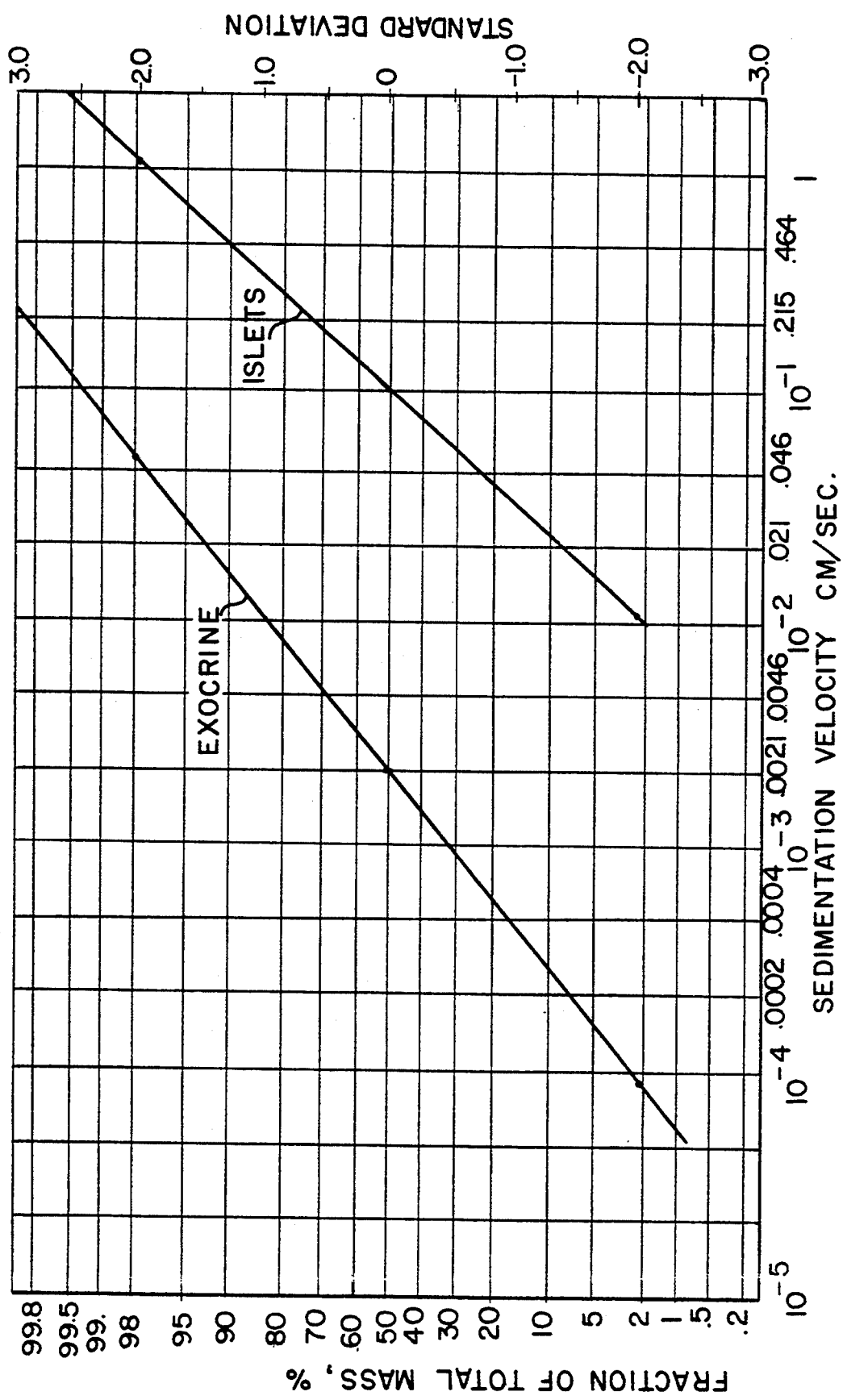
FIG. 4 shows the sedimentation velocities of islets and exocrine tissue for the hypothetical example herein.

With these assumptions, the size distributions (by mass) for islets and tissue are shown in FIG. 3. This also produces a log-normal sedimentation velocity distribution. The sedimentation velocities for islets and tissue are shown in FIG. 4.

Figure 5:
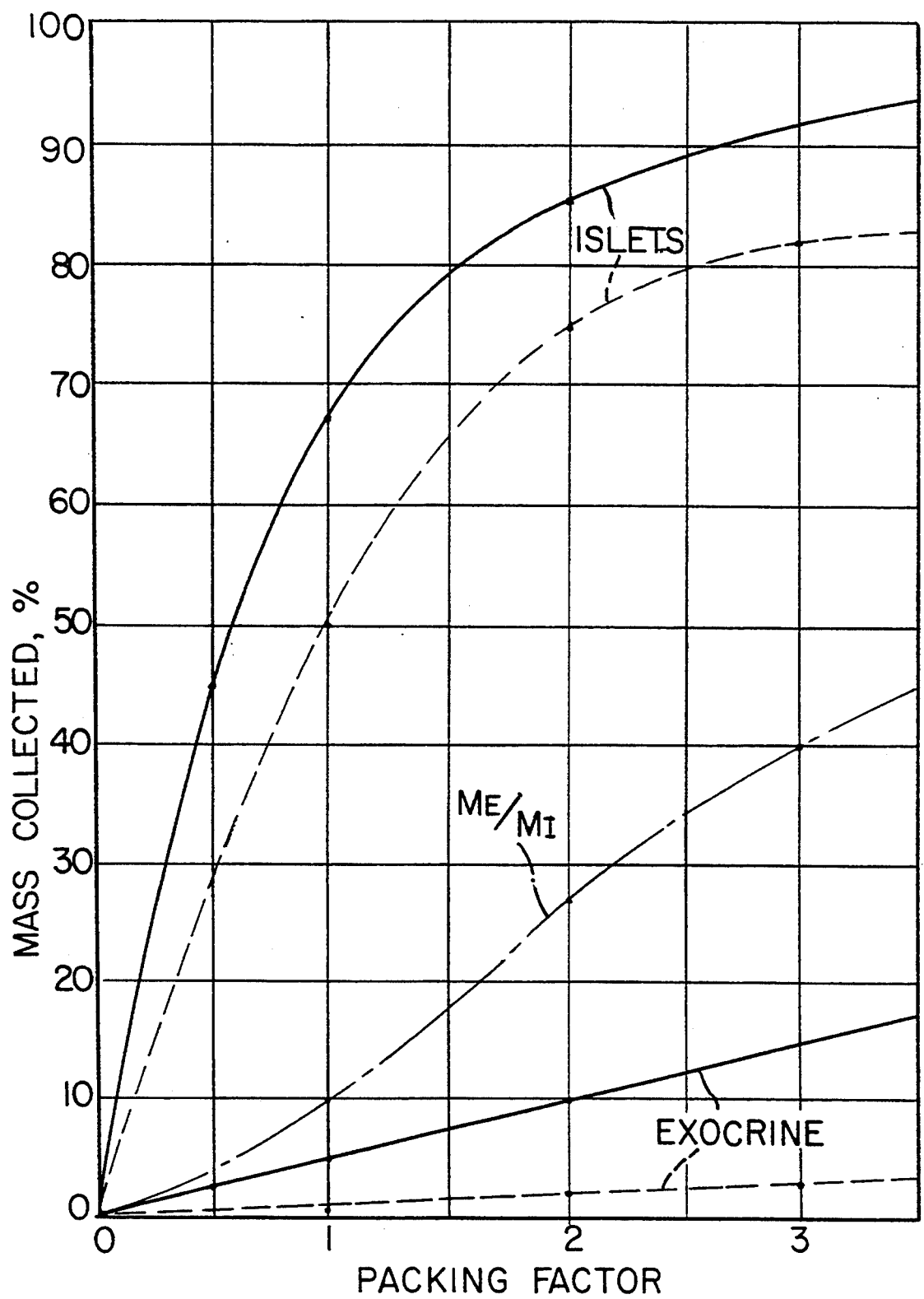
FIG. 5 shows the mass percentages of islets and exocrine tissue collected versus various packing factors for the hypothetical example herein.

FIG. 5 shows with the solid lines the percentage of islets and percentage of tissue collected, both expressed in terms of mass percentages rather than number percentages, versus average packing factor. It can be seen that at an average packing factor of 2, for example, roughly 85% of the mass of islets is collected while only about 27% of the mass of tissue is collected. It should be noted that since the unprocessed solution normally contains much more tissue than islets, even one or two orders of magnitude more, the collected mass still may contain more tissue than islets even though the collection rate of islets was much higher than the collection rate of tissue.

The collected mixture of tissue and islets can be reprocessed by introducing it into the top wall of the processing channel, with Hanks solution or a similar uncontaminated solution flowing through the channel. Under this procedure, it is important to introduce the mixture into the solution where laminar flow is established, and to do so without disrupting the laminar flow of the solution. This can be accomplished using a low-flow infusion inlet in the top of channel. The results of this reprocessing are shown by the dashed lines of FIG. 5 for various packing factors, and are summarized in the table below, in which $m_e/m_i$ is the ratio of mass of exocrine tissue collected to mass of islets collected.

| PF | % Islets | % Exocrine | $m_e/m_i$ |
|---|---|---|---|
| 1 | 50 | 0.5 | .10 |
| 2 | 75 | 2 | .27 |
| 4 | 83 | 4 | .48 |
| 8 | 85 | 6 | .71 |

What is claimed is:

1. A method of concentrating islets of Langerhans suspended in a liquid, comprising establishing laminar flow of the liquid through an elongated conduit with a first end and a second end, having a liquid inlet at the first end, and a liquid outlet at the second end, having a substantially constant cross sectional area, and having a floor to receive islets sedimenting from the liquid, the conduit being inclined such that the inlet is above the outlet, the conduit also having an islet collecting well depending from the floor; allowing the islets to sediment from the liquid into the well; and removing the islets from the well.

2. The method of claim 1, wherein said step of allowing the islets to sediment includes allowing the islets to sediment onto the floor and then move along the floor to the well.

3. The method of claim 1, further comprising further concentrating the islets removed from the well.

4. The method of claim 3, wherein said further concentrating is by at least one of centrifugation or filtering.

5. The method of claim 1, further comprising, prior to establishing laminar flow of the liquid, obtaining the islets suspended in the liquid by enzymatic digestion of a pancreas.

6. The method of claim 1, wherein the flow is controlled by flow control means.

7. The method of claim 6, wherein the flow control means includes at least one pump to pump solution through the conduit.

8. The method of claim 7, wherein the flow control means includes means for adjusting the flow through the outlet.

9. The method of claim 7, wherein the flow control means adjusts the flow based on at least one of: the concentration of islets in the liquid, the size of the islets in the liquid, the concentration of non-islet solids in the liquid, the size of non-islet solids in the liquid, and the amount of islets to be removed from the conduit.

10. The method of claim 7, wherein the pump is downstream from the outlet and there is no pump upstream from the inlet, so that the islets are not subjected to a pump.

11. The method of claim 1, wherein said step of establishing laminar flow produces a laminar flow portion in the conduit, and the period of time if takes for an average sized islet to flow through the laminar flow portion is greater than the period of time it takes for said islet to sediment to the floor, so that an average sized islet sediments to the floor before reaching the outlet.

12. The method of claim 11, wherein said period of time it takes for an average sized islet to flow through the laminar flow portion is at least twice the period of time it takes for an average sized islet to sediment to the floor.

* * * * *